(12) United States Patent
Sacherer

(10) Patent No.: US 7,961,303 B2
(45) Date of Patent: Jun. 14, 2011

(54) TEST TAPE UNIT FOR BLOOD TESTS

(75) Inventor: Klaus Dieter Sacherer, Kirchheim (DE)

(73) Assignee: Roche Diagnostics Operations, Inc., Indianapolis, IN (US)

( * ) Notice: Subject to any disclaimer, the term of this patent is extended or adjusted under 35 U.S.C. 154(b) by 691 days.

(21) Appl. No.: 11/775,438

(22) Filed: Jul. 10, 2007

(65) Prior Publication Data

US 2008/0049227 A1    Feb. 28, 2008

(30) Foreign Application Priority Data

Jul. 11, 2006  (EP) ...................................... 06014316

(51) Int. Cl.
*G01N 33/48* (2006.01)
(52) U.S. Cl. .......................................... 356/39; 356/42
(58) Field of Classification Search ............. 356/39–50, 356/440–444, 244–246; 422/82.05, 68.1, 422/99, 102–104, 58; 436/43–46, 55; 221/76, 221/79; 435/287.1–287.3
See application file for complete search history.

(56) References Cited

U.S. PATENT DOCUMENTS

| 3,972,778 | A | * | 8/1976 | Cunningham | ............. | 435/287.3 |
| 4,264,560 | A | * | 4/1981 | Natelson | ......................... | 422/58 |
| 4,941,742 | A | * | 7/1990 | Schrader et al. | ................ | 356/38 |
| 5,096,828 | A | * | 3/1992 | Ishizaka et al. | ................. | 436/44 |
| 5,630,986 | A |   | 5/1997 | Charlton et al. | | |
| 6,040,191 | A |   | 3/2000 | Grow | | |
| 2004/0048394 | A1 | | 3/2004 | Kirchhevel | | |
| 2005/0201897 | A1 | * | 9/2005 | Zimmer et al. | ............ | 422/82.05 |

FOREIGN PATENT DOCUMENTS

| DE | 639 177 | 11/1936 |
| EP | 1 424 040 | 6/2004 |
| WO | WO2005/047861 | 5/2005 |
| WO | WO2006/059232 | 6/2006 |

* cited by examiner

*Primary Examiner* — Gregory J Toatley
*Assistant Examiner* — Tri T Ton
(74) *Attorney, Agent, or Firm* — Bose McKinney & Evans LLP

(57) ABSTRACT

The present invention provides a test tape unit suitable for testing blood sugar. The test tape unit comprises an analytical test tape, a feed spool for unwinding unused test tape, a take-up spool for winding used test tape, and a tape guide to expose a section of test tape at a measuring site for receiving an application of body fluid. The tape guide has a flat support frame which stretches the test tape at the measuring site and forms the border of a measuring opening which is kept free from optical elements for producing an optical measurement.

59 Claims, 2 Drawing Sheets

TEST TAPE UNIT FOR BLOOD TESTS

RELATED APPLICATIONS

This application claims priority to EP 06 014 316.1, filed Jul. 11, 2006, which is hereby incorporated by reference in its entirety.

BACKGROUND

In the past, diabetics have used individual test strips for self-diagnosis in which the strips were analyzed photometrically after applying a small amount of blood to the strip to determine the glucose content of the fluid sample as accurately and reliably as possible. In order to improve the user-friendliness of this test system, it has been proposed that such testing be performed on a test tape in the form of a tape cassette. It is possible to insert tape cassettes as a disposable component into compact hand-held devices to automatically and rapidly carry out all required analytical steps. In these tape cassette testing systems, the disposable components are mass produced and high demand occurs due to the reliability.

Accordingly, document WO 2005/006985 discloses a test tape guide curved in an arch that exposes a section of test tape to receive an application of liquid on the front side and to perform an optical measurement on the rear side by means of a reflection-photometric measuring unit focusing on this area. However, with this arrangement having parallel arched rails, there is a risk that in the case of a thin flexible test tape the central tape area will arch inwards under tension in the free space between the rails and thereby making an accurate optical focus more difficult. Such tape deformation has already proven to be problematic in the case of small radii of curvature, especially with regard to measuring optics having a short focal distance.

In order to overcome this problem, it has been proposed that optical elements in the form of cylinder lens be used as an application tip, wherein the lens bundles the measuring light in the optical path of the photometer. However, just as in the case of simple optical windows, care must be taken that high quality requirements are achieved for the required measuring accuracy especially with regard to transmission, scratch resistance, temperature resistance, coefficient of expansion, optical quality, and other material parameters or faults such as those listed in International Standard ISO 10110.

SUMMARY OF INVENTION

Embodiments incorporating the present invention address the described disadvantages of the prior art and further improve test tape systems while being simple to manufacture, provide special application advantages and high measurement accuracy with a low strain on the test tape. In particular, these embodiments are arranged without an optical component or material window in the area of the tape guide and thus optical elements which interact or interfere with the passage of light are avoided.

One embodiment of the tape guide has a planar support frame which holds the test tape section flat at the measuring site, wherein the frame has legs that circumscribe or border a clear measuring opening which is kept free from optical elements for an optical measurement to be taken on the rear side of the tape. This provides good targeting accuracy and adequate support for the application of liquid on the front side of the tape, while the test tape is held in a narrowly defined measuring plane without significant or noticeable bending.

The "clear" measuring opening is provided as a simple optical entrance that allows light to be emitted into the opening and permits the passage of reflected radiation under constant conditions. According to this embodiment, it is unnecessary to manufacture special optical components such as lens, filters, or material windows. Also, by avoiding tape constriction, this embodiment provides an energy efficient and gentle tape transport.

In a similar embodiment, the frame legs of the support frame advantageously border the measuring opening in a rectangular shape and also provide sufficient space for several light beams oriented towards the test tape.

In another exemplary embodiment, the support frame has two parallel frame legs extending in the longitudinal direction of the test tape and the distance between the outer edges of these two legs is less than the width of the test tape. The portion of the test tape border that extends past the frame legs can thus provide a screen against contamination of the device by a sample of body fluid.

In another embodiment, the support frame has two parallel frame legs at right angles, or transverse, to the direction the test tape is transported, the length of which corresponds to at least the width of the test tape. This avoids tape constriction in the deflection area and supports planar frame stretching. These frame legs are referred to as "the transverse frame legs."

In order to further improve the tape guide, it is advantageous when the frame legs of the support frame, which support the test tape in its longitudinal direction, are flattened into a strip shape. It is also advantageous when the transverse frame legs are rounded at a deflecting edge for the test tape.

In another advantageous embodiment, the support frame is formed by a flat top surface of a truncated, pyramid-shaped projection of the tape guide. This projection is also referred to as being tapered at its top surface. This tapered projection improves handling and hygiene when applying liquid to the test tape.

For the application of body fluid to the test tape, it is advantageous when the tape guide has deflecting bevels adjoining the support frame in the longitudinal direction of the tape, wherein the deflecting bevels are positioned at an acute angle with the plane defined by the support frame.

In order to secure the test tape against lateral deflection, the tape guide can advantageously have side boundaries or walls which are arranged adjacently outside of the support frame so that the test tape can be precisely centered on the support frame.

In addition, it is advantageous when the test tape is unwound from the feed spool by driving the take-up spool. Also, to keep the test tape flat at the measuring site, the test tape should be held in tension by return forces of more than 1 N.

It is advantageous for mass production to occur when the support frame is molded as one piece onto a molded part. The molded part can be an injection-molded part consisting of polypropylene, whereby the optical area is screened against the entry of scattered external light by a black coloring.

If the body fluid sample application and measurement take place at the same site, transporting the test tape section to a distant measuring site is not necessary. In an exemplary embodiment, it is advantageous when the body fluid is applied to the front side of the test tape section, which is supported by the support frame, and a reflectometric measurement is taken from the rear side of the tape, which rests on the support frame, with free radiation through the measurement opening.

In order to simplify the use of the device, it is advantageous when a measuring chamber delimited by the tape guide is used with a measuring unit, wherein a light source and a light receiver of the measuring unit are focused above the measuring opening onto the test tape section that is located above it.

The tape guide is advantageously covered from the outside by a cover part or housing, wherein the support frame protrudes from an opening in the cover part or housing. A test tape unit is designed as a tape cassette for being inserted into a test device.

Embodiments incorporating the present invention also provide a test system comprising a reflectometric measuring unit, a tape drive, and a test tape unit which are inserted into a hand-held device.

BRIEF DESCRIPTION OF THE DRAWINGS

The above-mentioned aspects of the present invention and the manner of obtaining them will become more apparent and the invention itself will be better understood by reference to the following description of the embodiments of the invention, taken in conjunction with the accompanying drawings, wherein.

DETAILED DESCRIPTION

The embodiments of the present invention described below are not intended to be exhaustive or to limit the invention to the precise forms disclosed in the following detailed description. Rather, the embodiments are chosen and described so that others skilled in the art may appreciate and understand the principles and practices of the present invention.

Figure 1:
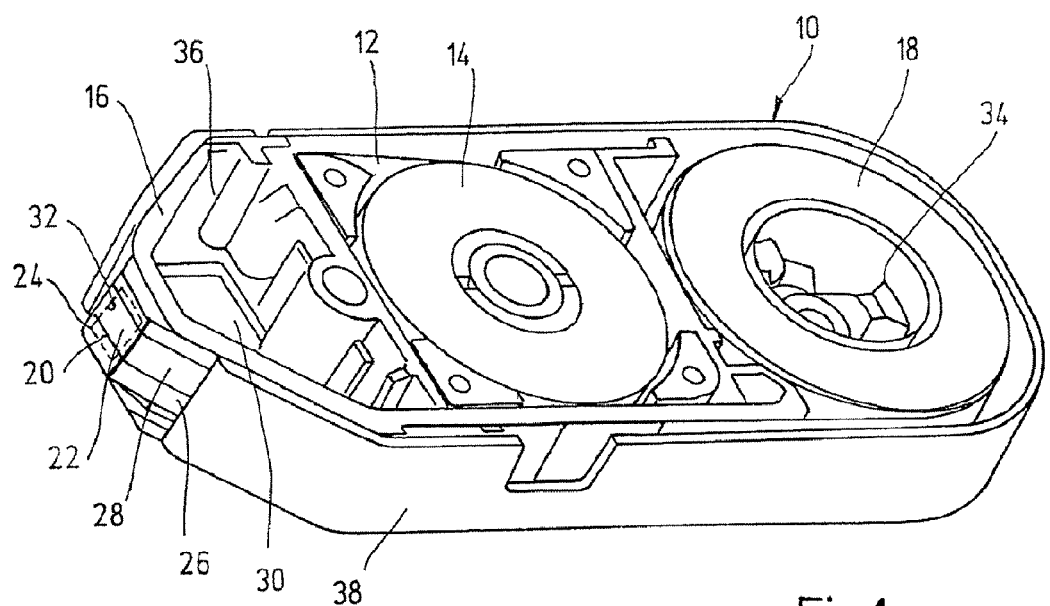
FIG. 1 is a perspective view of a tape cassette for blood testing in which an outer cover or housing is removed to illustrate the interior components of the cassette.

The tape cassette 10 shown in FIG. 1 enables large quantities of glucose analyses to be carried out on blood samples taken by a patient. In this exemplary embodiment, the tape cassette 10 comprises an analytical test tape 12 which is pulled from a feed spool 14 and wound over a tape guide 16 onto a take-up spool 18. A section of test tape 20 is stretched flat over a planar support frame 24 at a measuring site 22 in order to apply body fluid to the front side of the test tape 20 and take a precise reflectometric measurement on the rear side.

The test tape 12 consists of a light-permeable carrier tape 26 on the front side in which test fields or elements 28 are applied in sections as labels. These test fields or elements contain dry chemicals which respond to the analyte, such as glucose, in the body fluid and lead to a measurable change in the light that is reflected back when the rear side is illuminated. The carrier tape 26, for example, consists of a 5 mm wide and approximately 10 μm thick foil on the front side of which a detection film of 50 μm in thickness is applied in sections.

As the measurement is being taken, the measuring light is irradiated and reflected back through a measuring opening 32 bordered by the support frame 24 without optical elements such as lens, filters, or windows filled with material being present within the area of the opening, although the measuring opening can, optionally, be bordered by a diaphragm. This provides a defined rear-side focusing or alignment of the optical measuring unit on the test tape section 20 which is exposed flat over the measuring opening 32.

In order to transport the test fields or elements 28 successively to the measuring site 22, a tape drive engaging in the hub 34 of the take-up spool 18 enables the test tape 12 to be wound forward. In this embodiment, return forces of about 2 N are generated by friction on the feed spool 14 and in the area of the tape guide 16 (and especially at a passage seal 36) such that the test tape 12 is adequately placed under tension to ensure it lies flat on the support frame 24.

The tape guide 16 is formed by an injection molded part made of polypropylene and provides support for the spools 14, 18. A cover part or housing 38 is provided to cover the tape guide 16 from the outside and has an opening in a tapered narrow side wall for an easily accessible exposure of the support frame 24.

Figure 2:
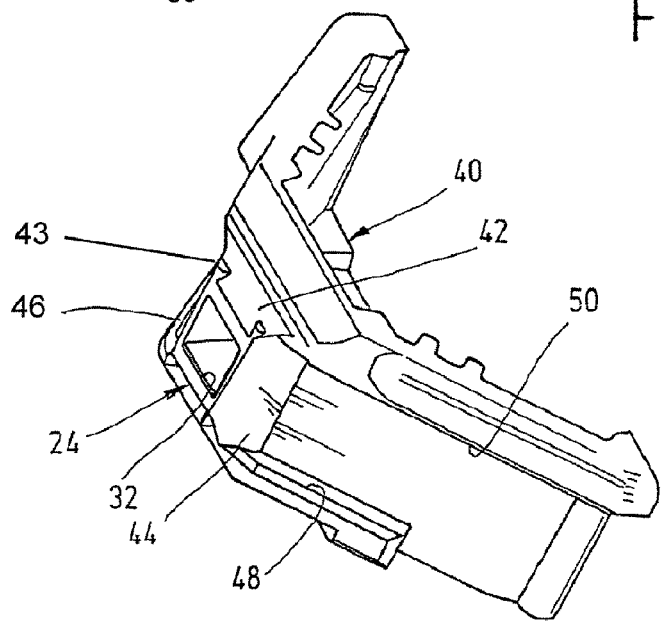
FIG. 2 is an enlarged perspective view of a head portion of the tape cassette of FIG. 1.

According to the embodiment shown in FIG. 2, the support frame 24 is formed on a head portion 40 of the tape guide 16. In this embodiment, the support frame 24 is formed at the flat top surface of a tapered projection 42 which has a truncated, pyramid-shape to facilitate a hygienic application of body fluid samples. Thus, in the longitudinal direction of the tape, deflecting bevels 44, 46 adjoin the support frame 24 to guide the test tape 12 along the opposing longitudinal sidewalls of the cassette 10. Side boundaries or walls 48, 50 are provided in this area which secure the test tape 12 from lateral deflection and prevent the test tape 12 from slipping sideways and off the support frame 24.

Figure 3:
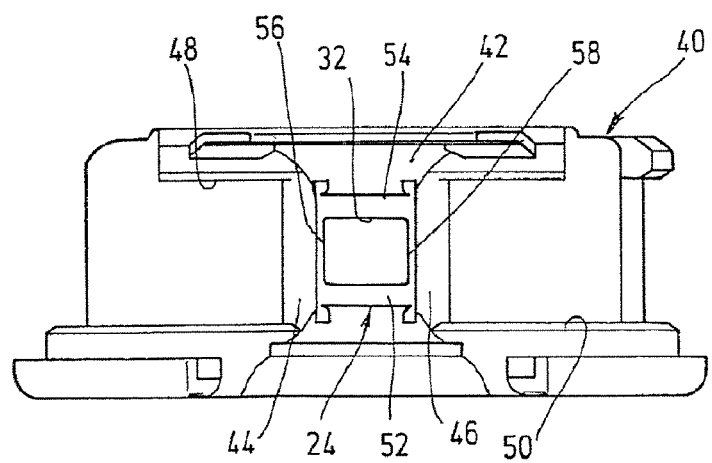
FIG. 3 is a top view of the head portion of FIG. 2.

According to the exemplary embodiment shown in FIG. 3, the support frame 24 has two frame legs 52, 54 extending longitudinally in the same direction as the test tape moves (left-to-right in FIG. 3) and two frame legs 56, 58 which are at right angles or transverse to frame legs 52, 54. The longitudinal frame legs 52, 54 lay flat and the distance between the outer edges of the legs 52, 54 is less than the width of the test tape 12. In this embodiment, the width of the test tape 12 extends past the sides of the legs 52, 54 and body fluid is prevented from reaching the projection 42 during application. The transverse frame legs 56, 58 are rounded off with a radius of approximately 0.3 mm at the deflecting edges 43 and their length is such that the entire width of the test tape 12 is supported thereon. With the test tape having a width of approximately 5 mm, the frame legs 56, 58 also have a length of 5 mm whereas the measuring opening 32 has a shorter length of 3 mm and width of 2 mm. This design of the support frame 24, in addition to allowing hygienic handling, also prevents the stretched portion of test tape 20 at the measuring site from arching or bending.

Figure 4:
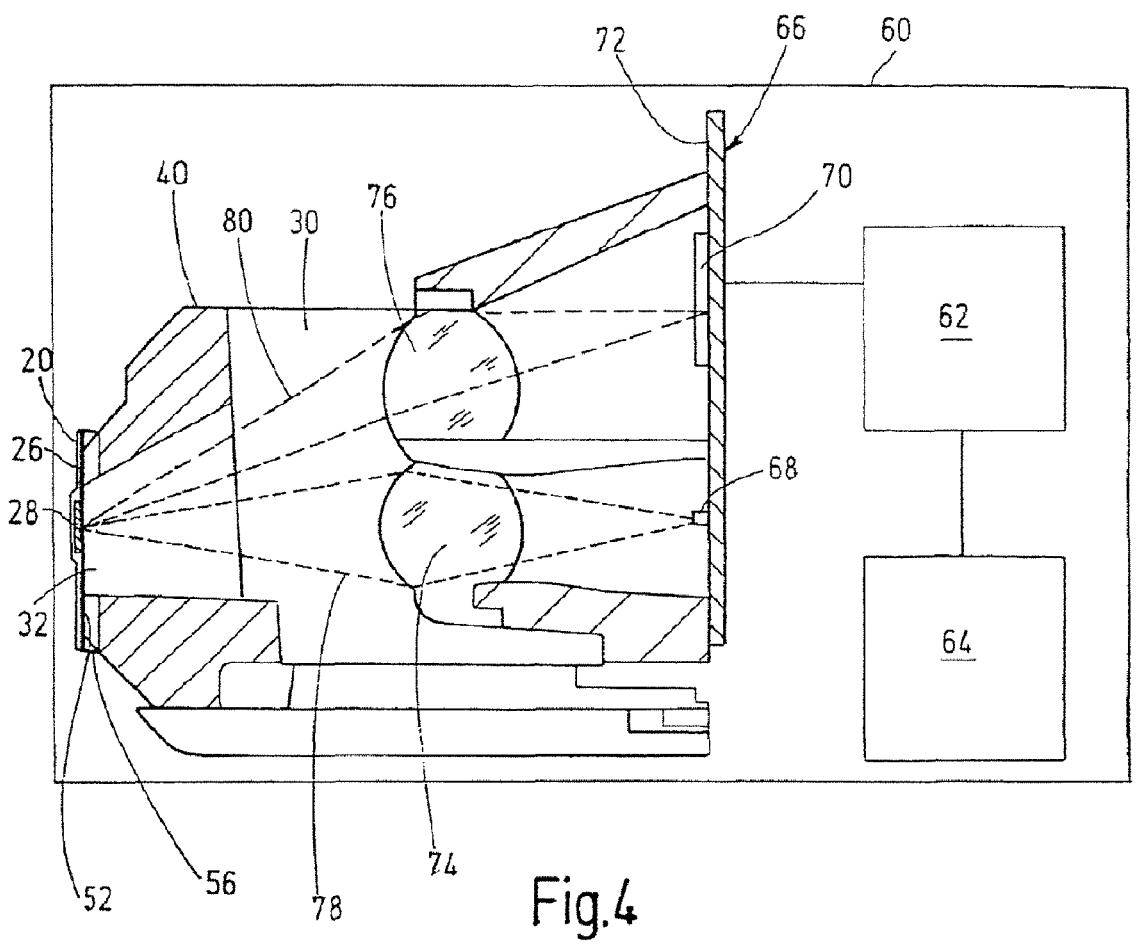
FIG. 4 is a partial schematic view of a test system with a tape cassette inserted therein.

In order to simplify handling the cassette 10, the cassette 10 is inserted into a hand-held device 60 as illustrated in FIG. 4. The device 60 has a control and evaluation unit 62, a tape drive 64 acting on the hub 34 of the take-up spool 18, and an optical measuring head 66 positioned in the measuring chamber 30 on the cassette side.

The measuring head 66 and the head portion 40 of the cassette 10 are shown in FIG. 4 in the transverse direction (i.e. to the right) from the test tape. The measuring head 66 comprises a light source 68 and a light receiver 70 on a printed circuit board 72. A pair of lens 74, 76 in the measuring head 66 focus the light source 68 and the light receiver 70 through the transparent carrier tape 26 onto the test field or element 28. In this embodiment, light beams 78, 80 on the transmission and receiving side pass through the measuring chamber 30 and, in particular, through the measuring opening 32 without any interaction or interference from optical components. This provides reflection-photometric detection in a defined measuring plane where the optical path is not adversely affected by components of the cassette 10.

While exemplary embodiments incorporating the principles of the present invention have been disclosed hereinabove, the present invention is not limited to the disclosed embodiments. Instead, this application is intended to cover any variations, uses, or adaptations of the invention using its general principles. Further, this application is intended to cover such departures from the present disclosure as come within known or customary practice in the art to which this invention pertains and which fall within the limits of the appended claims.

What is claimed is:

1. A test tape unit for testing blood, comprising:
   an analytical test tape;
   a feed spool configured for dispensing unused test tape and a take-up spool configured for receiving used test tape; and
   a tape guide adapted for positioning and exposing a section of the test tape at a measuring site, the tape guide comprising a planar support frame, the test tape being held in tension, wherein the section of test tape at the measuring site is held flat against the planar support frame, wherein the support frame comprises longitudinal and transverse frame legs circumscribing a measuring opening which is free from optical elements.

2. The test tape unit of claim 1, wherein the plurality of frame legs define a rectangle.

3. The test tape unit of claim 1, wherein two of the frame legs are substantially parallel to one another and extend in the longitudinal direction of the test tape.

4. The test tape unit of claim 3, wherein the distance between the outer edges of the two substantially parallel frame legs is less than the width of the test tape.

5. The test tape unit of claim 3, wherein the substantially parallel frame legs define a flat shape.

6. The test tape unit of claim 1, wherein the width of the measuring opening is 0.3 to 0.6 times the width of the test tape.

7. The test tape unit of claim 1, wherein the length of the measuring opening is one to two times the width of the measuring opening.

8. The test tape unit of claim 1, wherein two of the frame legs are substantially parallel to one another and extend transverse to the direction the test tape moves.

9. The test tape unit of claim 8, wherein the two substantially parallel frame legs are at least as long as the width of the test tape.

10. The test tape unit of claim 8, wherein the two substantially parallel frame legs are rounded at a deflecting edge.

11. The test tape unit of claim 1, wherein the tape guide comprises a tapered projection with a flat top surface defining the support frame.

12. The test tape unit of claim 1, wherein the tape guide has deflecting bevels adjoining the support frame and oriented along the direction the test tape moves, the deflecting bevels being disposed at an acute angle of 70° to 85° from the plane formed by the support frame.

13. The test tape unit of claim 1, wherein the tape guide comprises side boundaries configured to prevent lateral deflection of the test tape.

14. The test tape unit of claim 1, wherein the test tape is configured for being dispensed from the feed spool by driving the take-up spool, the test tape being held under tension by return forces greater than 1 N.

15. The test tape unit of claim 1, wherein the support frame is integrally formed.

16. The test tape unit of claim 14, wherein the support frame comprises black polypropylene.

17. The test tape unit of claim 1, wherein the front side of the test tape is configured for receiving body fluid to be analyzed.

18. The test tape unit of claim 1, wherein the test tape is arranged on the support frame such that radiation is transmitted onto the rear side of the test tape through the measuring opening for a reflectometric measurement.

19. The test tape unit of claim 1, further comprising a measuring chamber defined by the tape guide and configured to be used with a measuring unit, wherein the measuring unit comprises a light source and a light receiver which are focused through the measuring opening onto the section of test tape positioned over the measuring opening.

20. The test tape unit of claim 1, further comprising a housing that partially encloses the tape guide, wherein the support frame protrudes from an opening in the housing.

21. The test tape unit of claim 1, wherein the test tape unit comprises a tape cassette configured to be removably received in a test device.

22. A test system for optical testing of a body fluid sample, comprising:
   a housing;
   a tape drive and an optical measuring unit disposed in the housing; and
   a test tape unit removably receivable in the housing, comprising:
   an analytical test tape;
   a feed spool configured for dispensing unused test tape and a take-up spool configured for receiving used test tape; and
   a tape guide adapted for positioning and exposing a section of the test tape at a measuring site, the tape guide comprising a planar support frame, the test tape being held in tension, wherein the section of test tape at the measuring site is held flat against the planar support frame, wherein the support frame comprises longitudinal and transverse frame legs bordering a measuring opening which is free from optical elements.

23. The test system of claim 22, wherein the tape drive is configured to drive the take-up spool as the test tape is held under tension by return forces greater than 1 N.

24. The test system of claim 22, wherein the measuring unit is configured to optically scan the test tape at the measuring site by producing at least one light beam that passes through the measuring opening.

25. The test system of claim 22, wherein the measuring unit comprises a light source and a light receiver, the light source being arranged to transmit light through the measuring opening onto the rear side of the test tape and the light receiver being arranged to receive light through the measuring opening from the rear side of the test tape.

26. A method of using a test system of the type having a tape cassette including a test tape carrying a plurality of test elements and a measuring site having a measuring opening at which the test elements are analyzed, the measuring site comprising a planar support frame which holds the section of test tape at the measuring site flat, the support frame comprising longitudinal and transverse frame legs bordering the measuring opening, the method comprising:
   advancing a section of the test tape having a test element to the measuring site;
   holding the section of the test tape in tension flat against the planar support frame and aligning the test element over the measuring opening;

applying a body fluid sample to the test element;
projecting light through the measuring opening onto the rear side of the section of the test tape and detecting light that is reflected back through the measuring opening, wherein the projected and reflected light is passed through the measuring opening without interaction with or interference from optical components; and
correlating the detected light to presence or concentration of an analyte in the body fluid sample.

27. The method of claim 26, further comprising holding the section of the test tape under tension with a force greater than 1 N.

28. The method of claim 27, further comprising generating the force by providing friction from a feed spool.

29. The method of claim 26, wherein the step of applying a body fluid sample to the test element is performed after the step of advancing the section of the test tape having a test element to the measuring site.

30. The method of claim 26, further comprising providing the planar support with two frame legs which extend substantially parallel to the direction the test element moves, the holding step further comprising positioning the edges of the test tape past the two substantially parallel frame legs to prevent body fluid from spreading beyond the section of the test tape.

31. The method of claim 26, further comprising advancing the test tape along a tape guide and holding a second section of the test tape flat and aligning a second test element over the measuring opening.

32. The method of claim 31, further comprising holding the second section of the test tape flat by providing friction from a supply spool.

33. The method of claim 31, further comprising advancing the test tape by driving a take-up spool.

34. The method of claim 26, further comprising providing the section of the test tape with a light-permeable layer on the rear side thereof and the test element arranged on the front side of the light-permeable layer.

35. The method of claim 26, further comprising advancing the section of the test tape from the measuring site to a take-up spool.

36. The method of claim 26, further comprising advancing the test tape along a tape guide and preventing lateral deflection of the section of the test tape with side boundaries disposed on the tape guide.

37. A test system for analyzing analytical test tape to determine presence or concentration of a substance in a body fluid, comprising:
a tape guide configured to guide and hold test tape as it is advanced during use of the unit; and
the tape guide comprising a measuring site at which test elements of the test tape are evaluated, the measuring site comprising a planar support, the support comprising transverse and longitudinal frame legs bordering a measuring opening that is free of optical elements, the planar support configured to hold a section of the test tape in tension and flat against the planar support, and the measuring opening configured to allow light to pass through the opening without interaction with or interference from optical components.

38. The test system of claim 37, wherein the tape guide comprises a tapered projection.

39. The test system of claim 38, wherein the top surface of the tapered projection defines the planar support.

40. The test system of claim 37, wherein the planar support comprises frame legs which border the measuring opening.

41. The test system of claim 40, wherein two of the frame legs extend substantially parallel to the direction in which the tape guide advances the test tape.

42. The test system of claim 41, wherein the distance between the outer edges of the two substantially parallel frame legs is less than the width of the test tape.

43. The test system of claim 40, wherein two of the frame legs are substantially parallel to one another and extend transverse to the direction in which the tape guide advances the test tape.

44. The test system of claim 37, wherein the tape guide holds the test tape under tension with a force greater than 1 N.

45. The test system of claim 37, wherein the tape guide comprises side boundaries configured to prevent lateral deflection of the test tape.

46. The test system of claim 37, further comprising a housing for containing the tape guide, wherein the housing includes an opening through which the planar support protrudes.

47. The test system of claim 46, further comprising a tape drive disposed in the housing.

48. The test system of claim 47, further comprising a take-up spool removably receivable in the housing and configured for receiving used test tape.

49. The test system of claim 16, further comprising a measuring unit configured to optically evaluate a section of the test tape positioned at the measuring site.

50. The test system of claim 49, wherein the measuring unit produces light that passes through the measuring opening.

51. The test system of claim 49, wherein the measuring unit comprises a light source and a light receiver, the light source being arranged to transmit light onto the rear side of the test tape through the measuring opening and the light receiver being arranged to receive light deflected from the rear side of the test tape through the measuring opening.

52. The test system of claim 51, wherein the measuring unit further comprises a first lens for focusing the transmitted light and a second lens for focusing the reflected light.

53. The test system of claim 50, wherein the measuring unit further comprises an evaluation unit for evaluating the light reflected from the rear side of the test tape.

54. The test system of claim 46, further comprising a feed supply removably disposed within the housing and configured for dispensing unused test tape.

55. The test tape unit of claim 1, wherein the longitudinal frame legs are flattened.

56. The test tape unit of claim 55, wherein the transverse frame legs are rounded at a deflecting edge thereof.

57. The test tape unit of claim 1, wherein the transverse frame legs are rounded at a deflecting edge thereof.

58. The test tape unit of claim 1, wherein the transverse and longitudinal frame legs define a rectangular opening.

59. The test tape unit of claim 1, wherein the frame is rectangular.

* * * * *